US011352388B2

(12) United States Patent
Hall et al.

(10) Patent No.: US 11,352,388 B2
(45) Date of Patent: Jun. 7, 2022

(54) METHOD FOR CHROMATOGRAPHY

(71) Applicant: Cytiva BioProcess R&D AB, Uppsala (BE)

(72) Inventors: Martin Hall, Uppsala (BE); Mikael Berg, Uppsala (BE); Ida Eklind, Uppsala (SE); Sandeep Kristiansson, Uppsala (BE)

(73) Assignee: Cytiva BioProcess R&D AB, Uppsala (SE)

( * ) Notice: Subject to any disclaimer, the term of this patent is extended or adjusted under 35 U.S.C. 154(b) by 87 days.

(21) Appl. No.: 15/564,224

(22) PCT Filed: Apr. 4, 2016

(86) PCT No.: PCT/EP2016/057351
§ 371 (c)(1),
(2) Date: Oct. 4, 2017

(87) PCT Pub. No.: WO2016/162308
PCT Pub. Date: Oct. 13, 2016

(65) Prior Publication Data
US 2018/0127459 A1 May 10, 2018

(30) Foreign Application Priority Data
Apr. 10, 2015 (GB) ..................... 1506113

(51) Int. Cl.
*C07K 1/18* (2006.01)
*B01D 15/36* (2006.01)
*C07K 14/755* (2006.01)
*A61K 38/37* (2006.01)
*A61P 7/00* (2006.01)
*A61K 38/00* (2006.01)

(52) U.S. Cl.
CPC .................. *C07K 1/18* (2013.01); *A61P 7/00* (2018.01); *B01D 15/363* (2013.01); *C07K 14/755* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,721,572 A | 1/1988 | Jordan | |
| 5,457,181 A | 10/1995 | Michalski et al. | |
| 7,208,093 B2 | 4/2007 | Berg et al. | |
| 8,329,871 B2 | 12/2012 | Borgvall et al. | |
| 2008/0207878 A1 | 8/2008 | Michel et al. | |
| 2010/0305305 A1 | 12/2010 | Poulle et al. | |
| 2011/0155668 A1 | 6/2011 | Glad et al. | |
| 2012/0122179 A1 | 5/2012 | Perret et al. | |
| 2014/0154233 A1 | 6/2014 | Pham et al. | |
| 2016/0024180 A1 | 1/2016 | Schroeder | |

FOREIGN PATENT DOCUMENTS

| | | | | |
|---|---|---|---|---|
| CN | 102584983 A | 7/2012 | | |
| EP | 0408029 A1 | 1/1991 | | |
| EP | 0 600 480 A2 | 12/1993 | | |
| WO | 2008/135568 A1 | 11/2008 | | |
| WO | 2009/007451 A1 | 1/2009 | | |
| WO | 2009/131526 A1 | 10/2009 | | |
| WO | 2010/005364 A1 | 1/2010 | | |
| WO | WO-2011102790 A1 * | 8/2011 | ........ | B01J 20/28004 |
| WO | 2012/134381 A1 | 10/2012 | | |
| WO | 2014/085861 A1 | 6/2014 | | |
| WO | WO-2014188313 A1 * | 11/2014 | ............... | C12N 9/52 |

OTHER PUBLICATIONS

Burnouf-Radosevich, T., et al. 1992 Vox Sang 62: 1-11. (Year: 1992).*
Burnouf, T., et al. 1991 Vox Sang 60: 8-15. (Year: 1991).*
Ruggeri, Z.M., et al. 1993 FASEB J 7: 308-316. (Year: 1993).*
PCT International Search Report and Written Opinion for PCT Application No. PCT/EP2016/057351 dated May 23, 2016 (10 pages).
GB Search Report for GB Application No. 1506113.8 dated Jan. 5, 2016 (5 pages).
Anonymous, "Simplified Purification During Vaccine Production," Ip.com, 2013, pp. 1-10.
Poster #10, "Colloids and Surfaces in Biologicay and Biomaterials—A Symposium on Surface and Materials Chemistry," Uppsala, Sweden, Nov. 4-6, 2015 (70 pages).
"Multimodal Chromatography—Handbook GE Healthcare Life Sciences Imagination at Work Multimodal Chromatography Handbook," 2013, https://www.gelifesciences.com/gehcls_images/gels/relatedcontent/files/1384943366025/litdoc29054808201 31220222224.pdf.
Chinese Office Action for CN Application No. 201680020792.6 dated Jul. 21, 2020 (37 pages, with English translation).
Jun et al., "Preliminary Research of Preparation of Highly Purified Human Plasma Factor IX with Conventional Chromatography," Pharmaceutical Biotechnology, 1999, 6(2):107-109 (English abstract).
Ribeiro et al., "Anion-Exchange Purification of Recombinant Factor IX from Cell Culture Supernatant Using Different Chromatography Supports," Journal of Chromatograph B, 2013, 938:111-118.
Zhu et al., Molecular Biology and Diseases, 1994 (15 pages).
Japanese Office Action for JP Application No. 2017-550147 dated Feb. 25, 2020 (10 pages with English translation).
Darcy et al., Methods Mol Biol., 2011, 681:369-82.
PCT International Search Report and Written Opinion for PCT Application No. PCT/EP2016/057356 dated Jun. 27, 2016 (13 pages).
GB Search Report for GB Application No. 11506117.90 dated Jan. 19, 2016 (4 pages).
Non-Final Office Action for U.S. Appl. No. 15/564,232 dated Sep. 30, 2020 (16 pages).

* cited by examiner

*Primary Examiner* — Marsha Tsay
(74) *Attorney, Agent, or Firm* — Eversheds Sutherland (US) LLP

(57) ABSTRACT

The present invention relates to the field of chromatography. More closely, the invention relates to a chromatographic method for purification of Factor VIII and von Willebrand factor from a cryoprecipitate of plasma. The chromatographic method is performed on a matrix comprising an inner porous core and outer porous lid surrounding said core.

12 Claims, 2 Drawing Sheets

METHOD FOR CHROMATOGRAPHY

CROSS REFERENCE TO RELATED APPLICATIONS

This application claims the priority benefit of PCT/EP2016/057351 filed on Apr. 4, 2016 which claims priority benefit of Great Britain Application No. 1506113.8 filed Apr. 10, 2015. The entire contents of which are hereby incorporated by reference herein.

FIELD OF THE INVENTION

The present invention relates to the field of chromatography. More closely, the invention relates to a chromatographic method for separation of Factor VIII/von Willebrand factor from a cryoprecipitate of plasma. The chromatographic method is performed on a matrix comprising an inner porous core and outer porous lid surrounding said core.

BACKGROUND OF THE INVENTION

Blood contains different types of cells and molecules which are necessary for vital body functions, and is therefore collected for therapeutic purposes, e.g. for blood transfusions.

However, it is possible to separate and prepare different fractions from blood, such as red blood cells or cell-free plasma, which enables a more directed therapeutic treatment of medical conditions. Several proteins in plasma can also be further isolated and used for specific therapeutic treatments, e.g. albumin is used to restore blood volume, immunoglobulins are used for immune deficiencies, and coagulation factors are used for blood coagulation disorders.

Plasma contains proteins of different function, different size, different amount, etc, so there are different methods for purification of the different plasma proteins. The purification processes are often designed to obtain several target proteins from one single starting pool of plasma. The processes typically involve precipitation or chromatography steps or a combination thereof.

Chromatography is often used to increase the purity of the target protein and reduce the risk for detrimental side effects. Many plasma proteins exhibit very potent activities, and if present as contaminants, they can cause adverse reactions even at very low levels, when administered to patients.

Collected human plasma is stored frozen, and the initial step in a plasma protein purification process is thawing and pooling of plasma. When thawing at low temperatures, typically 1-6 degrees C., some plasma proteins precipitate and can be collected by e.g. centrifugation. The collected precipitate is called cryoprecipitate, and can be used as a source of e.g. coagulation Factor VIII (FVIII) and von Willebrand Factor (vWF). Most of the FVIII in plasma is present as a complex with the large vWF multimers, and the two proteins are therefore often co-purified. The remaining liquid after removal of the cryprecipitate is often referred to as cryodepleted plasma or cryosupernatant, and this can be used as a source of e.g. albumin, immunoglobulin G (IgG), coagulation Factor IX (FIX).

The purification of many plasma proteins can be challenging. This can depend on the presence of small amounts of contaminants with undesired but potent activity, or that the proteins sometimes lose their activity or gain unwanted activity. For example, the FVIII easily loses activity, and the known methods used for purification are not satisfactory in many respects. Thus, there is a need of improved methods which can be operated at conditions where the proteins retain their activity, in order to obtain plasma products in good yields.

SUMMARY OF THE INVENTION

The present invention provides chromatographic materials and methods for purification of plasma proteins, especially for human plasma applications, wherein the purification can be achieved in fewer steps than in prior art. The chromatographic materials are capable of separations based on different principles, eg size and bind/elute. The method of the invention is especially suitable for sensitive plasma samples which comprise large proteins (eg FVIII/vWF) to be separated from smaller plasma proteins (HSA, IgG, FIX).

Thus, the present invention provides a chromatographic method for purification of Factor VIII (FVIII) and von Willebrand factor (vWF) from a cryoprecipitate of plasma, comprising the following steps: loading the cryoprecipitate on a chromatography column packed with a resin comprising porous lid beads (also called shell beads) having an inner porous core and an outer porous lid, wherein the inner core is provided with octylamine ligands and the lid is inactive (ie not provided with any ligands) and wherein the porosity of the lid and core does not allow entering of molecules larger than 500 kD, such as FVIII/vWF; adsorbing undesired plasma proteins (HSA, IgG, FIX being smaller that FVIII/vWF) on the ligands in the core; and collecting FVIII and vWF (FVIII/vWF complex, and FVIII, vWF) from the column.

Preferably the FVIII and vWF fractions are collected in flow through fractions from the column. Undesired plasma proteins are removed from the core by a cleaning in place (CIP) procedure.

In a preferred embodiment the shell is provided with anion exchange ligands and the method comprising a step of adsorbing FVIII/vWF on said anion exchange ligands and in the same step adsorbing the undesired proteins on the octylamine ligands in the core; and eluting FVIII/vWF from said anion exchange ligands. As will be shown below, the chromatogram results in a very sharp peak of FVIII/vWF well separated from the flow through.

The anion exchange ligands are preferably selected from diethylaminoethyl (DEAE), quaternary aminoethyl (QAE) or quaternary ammonium (Q), most preferably the anion exchange ligands are Q-ligands.

In a preferred embodiment the total shell bead (i.e. shell plus core) thickness is preferably 40-100 μm in diameter, and the lid thickness is preferably 2-10 μm.

The ligand concentration in the shell is preferably 10-50 μmole/ml.

In the above method for purification of FVIII/vWF the undesired plasma proteins are human serum albumin (HSA), IgG and Factor IX (FIX).

The porous material used in the method of the invention is preferably a sieving material, such as a gel filtration material commonly used for chromatography. The porous material in the inner core may have the same or different porosity as the porous material in the lid. The porous material is derived from a synthetic polymer material, such as styrene or styrene derivatives, divinylbenzene, acrylamides, acrylate esters, methacrylate esters, vinyl esters and vinylamides, or from a natural polymer material, such as carbohydrate material selected from agarose, agar, cellulose, dextran, chitosan, konjac, carrageenan, gellan and alginate. The preferred porous material is agarose.

In one embodiment the shell and core are made of agarose of the same porosity. In other embodiments the porosity of the shell is larger than of the core or the porosity of the shell is smaller than of the core.

In a second aspect, the invention relates to use of FVIII/vWF obtained from the above method for therapy for example albumin is used to restore blood volume, immunoglobulins are used for immune deficiencies, and coagulation factors are used for blood coagulation disorders.

It is contemplated that the FVIII/vWF fraction can be used for therapy without further purification from contaminants, but with necessary adjustments for biocompatibility etc. As will be shown below FVIII/vWF elutes in a very sharp peak with high purity and high activity.

Absorbance 280 nm—solid line; conductivity—dotted line; pH—dashed line.

Figure 2:
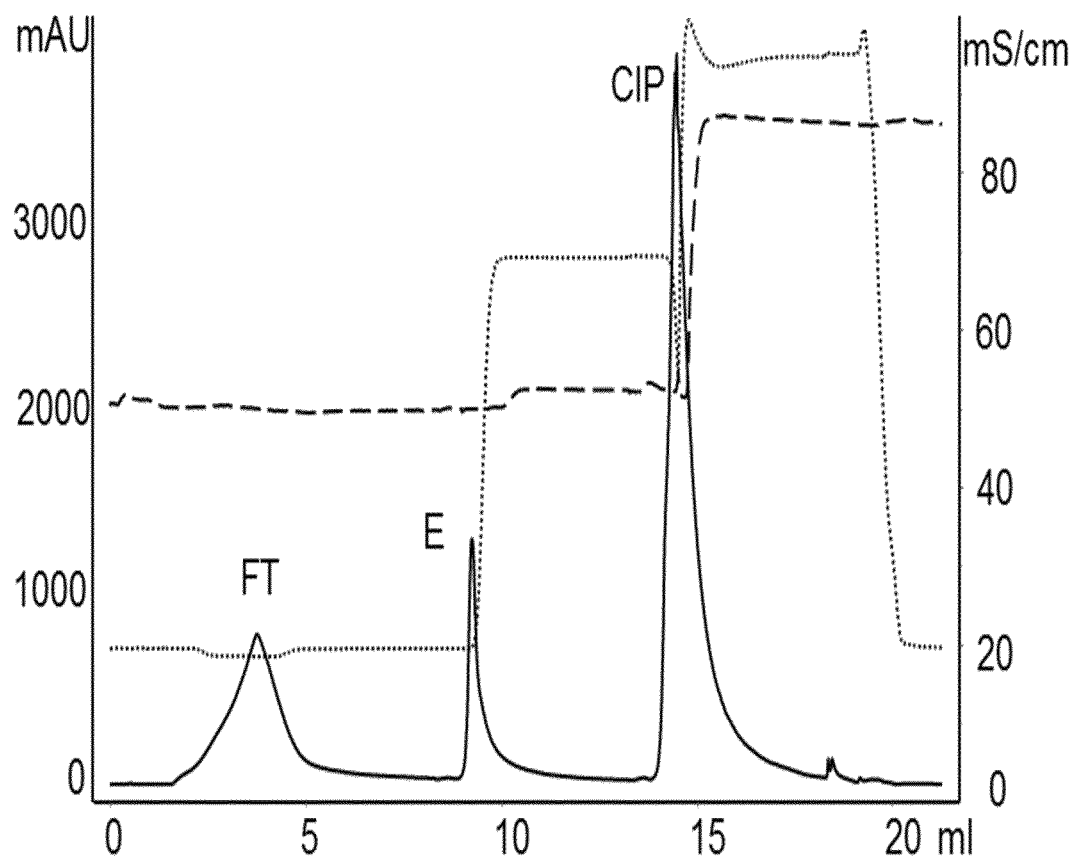

FIG. 2: Chromatogram of a cryoprecipitate applied to a prototype 59A column. FT=flow through peak; E=elution peak; CIP=cleaning-in-place peak.

Absorbance 280 nm—solid line; conductivity—dotted line; pH—dashed line.

DETAILED DESCRIPTION OF THE INVENTION

The invention will now be described more closely in connection with some non-limiting examples and the accompanying figures.

Experimental Section

Chromatographic Materials

The present invention describes plasma purification (in Example 2-3 below) of two chromatographic materials:

Capto Core 700 (GE Healthcare Bio-Sciences AB).

Prototype 59A, the synthesis of which will be described below in Example 1.

Example 1: Synthesis of Prototypes

Volumes of matrix refer to settled bed volume and weights of matrix given in gram refer to suction dry weight. For large scale reaction stirring is referring to a suspended, motor-driven stirrer since the use of magnet bar stirrer is prompt to damage the beads. Conventional methods were used for the analysis of the functionality and the determination of the degree of allylation, or the degree of ligand content on the beads.

The support particles used were highly crosslinked agarose beads, prepared according to the methods described in U.S. Pat. No. 6,602,990, which is hereby incorporated by reference in its entirety. The beads had a volume-weighted average diameter (D50,v) of 88 micrometers and a pore size distribution such that 69% of the pore volume was available to dextran molecules of Mw 110 kDa. This can also be expressed such that Kd for dextran 110 kDa on the beads was 0.69, when measured according to the methods described in "Handbook of Process Chromatography, A Guide to Optimization, Scale-Up and validation" (1997) Academic Press, San Diego. Gail Sofer & Lars Hagel eds. ISBN 0-12-654266-X, p. 368.

Allylation (Prototype 80)

300 mL (g) of support particles were washed 6× gel volumes (GV) with distilled water and then 3×GV with 50% NaOH. The gel was then sucked dry and transferred to a 2000 mL round bottom flask. 581.25 mL of 50% NaOH was added, mechanical propeller stirring was applied and the flask was immersed into a water bath at 50° C. After 30 minutes 96 mL of allyl glycidyl ether (AGE) was added. The reaction progressed for 17 h. The gel was washed 1×GV with distilled water, 5×GV with ethanol and then 8×GV with distilled water.

The allyl content, 239 µmol/mL, was measured by titration.

Partial Activation (Prototype 03)

96 g (mL) of allylated base matrix (prototype 80) were transferred drained to a 2000 mL round-bottomed flask. 864 mL of distilled water was added and mechanical stirring was applied. A solution of 475.7 µL bromine in 100 mL of water was prepared. The bromine solution (equivalent to the allyls in a 7 µm shell) was added slowly by using a dropping funnel during approximately 5 minutes. After the addition the suspension was still white. After 20 minutes the gel was washed with 10×1 GV with distilled water.

Determination of the Thickness of the Lid 6 g (mL) of partially activated gel from above were transferred drained into a 50 mL falcon tube. 5.49 g of distilled water and 0.634 mL of 50% NaOH were added and the tube was put into a shaking table at 50° C. and 750 rpm. The reaction progressed for 17 h. The gel was then washed 10×1 GV with distilled water. The remaining allyl content, 181 µmol/mL, was measured by titration. This corresponds to a theoretical shell thickness of 3.9 µm.

Q Coupling 30 mL of the partially activated gel from above and 22.8 mL of distilled water were transferred to a 100 mL round-bottom flask. 200 µL trimethyl ammonium chloride (TMAC) was added and the pH was adjusted to 11-11.5 by adding 50% NaOH. The reaction was stirred at 250 rpm at 30° C. for 17 h. The reaction was neutralized by adding 60% acetic acid to pH 5-7 before transferring to a glass filter (por. 3). The gel was washed with distilled water 10×1 GV, followed by 20% EtOH 2×1 GV. Titration of ion exchange groups gave a Q ligand density of 25.8 µmol/ml Prototype 59A Activation of Core Allyl 25 g (mL) of prototype 03 were transferred drained into a 100 mL round bottom flask with 12.5 mL of water and 0.17 g of sodium acetate trihydrate. Mechanical propeller stirring was applied (250 rpm). 375 µL of bromine was then added and the reaction was stirred for 15 min. The reaction had a persistent yellow colour. 4 g of sodium formate was added to quench the excess of bromine. The reaction was now white and the reaction was stirred again for 15 min before it was washed by 5×1 GV with distilled water.

Octylamine Coupling 24 g (mL) of the core activated gel from above were transferred drained into a 100 mL round bottom flask with 22.32 mL of water. Mechanical propeller stirring was applied (250 rpm). The flask was immersed into a water bath at 50° C. 88 µL of 50% NaOH was added and after 1 min 1.995 mL of octylamine was added and the reaction progressed for 17 h. The gel was washed by 3×1 GV with distilled water, 6×1 GV with ethanol, 6×1 GV with distilled water and then by 5×1 GV 20% ethanol. Titration of ion exchange groups gave a total ionic ligand density of 77.3 µmol/ml. The core ligand density was obtained by subtracting from this value the ligand density of the Q groups. The ligand density for the octylamine groups was calculated to be of 51.5 µmol/ml.

Ligands on CaptoCore 700 and Prototype 59A

Table 1 shows the lid thickness, ligand type and concentration in core and lid, respectively.

TABLE 1

| Resin | Lid thickness (µm) | Lid ligand (type, conc.) | Core ligand (type, conc.) |
|---|---|---|---|
| Capto Core 700 | 3.5–7.0 | No ligand | Octylamine, 40–85 µmol/ml |
| Prototype 59A | 3.9 µm | Q, 25.8 µmol/ml | Octylamine, 51.5 µmol/ml |

Buffers and Running Conditions

Chromatography system: ÄKTAexplorer 100

Column: HiScreen Capto Core 700, column volume (CV) 4.7 mL.

Flow rate 2.33 mL/min.

Sample: 10 mL dissolved cryoprecipitate.

Running buffer: 20 mM Na-citrate, 0.15 M NaCl, 2.6 mM CaCl2, pH 7.0.

Cleaning-in-place (CIP): 1 M NaOH, 30% isopropanol.

The column was equilibrated with running buffer prior to the sample application. 10 mL of dissolved cryoprecipitate was applied to the column, followed by 5 CV of running buffer. The column was then subjected to CIP by applying 5 CV of 1 M NaOH, 30% isopropanol. Finally, the CIP solution was washed out by 3 CV of running buffer.

Analyses

The cryoprecipitate and the collected flow through material were analyzed for FVIII (Chromogenix Coamatic Factor VIII kit), vWF (Technozym vWF:Ag ELISA kit), and FIX activity (ROX Factor IX kit). The fractions were also analyzed by SDS PAGE and liquid chromatography-mass spectrometry (LC-MS). Material which bound to the octylamine ligand in the core was eluted with the CIP solution and was not analysed.

Results

Figure 1:
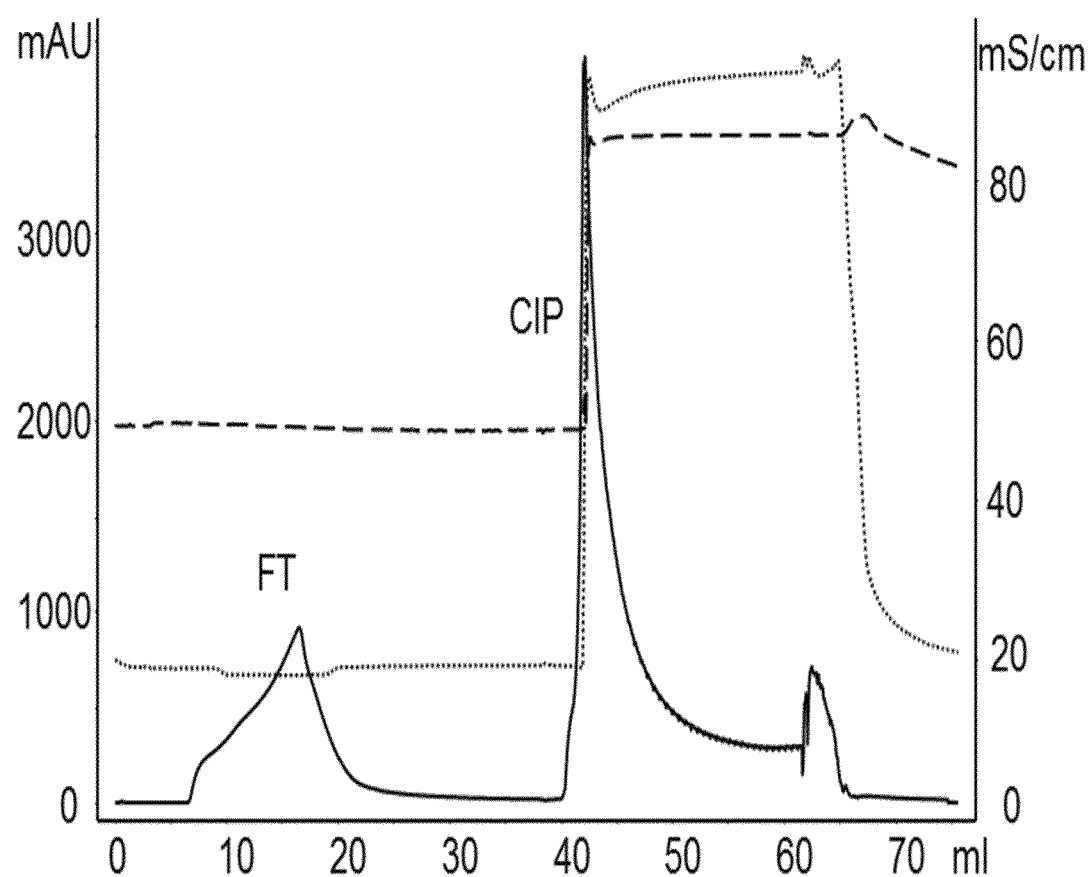
FIG. 1: Chromatogram of a cryoprecipitate applied to Capto Core 700 column. FT=flow through peak; CIP=cleaning-in-place peak.

See FIG. 1 for chromatogram and Table 2 for activity results and yield calculations. The FVIII yield was 80% and the vWF yield was 76% in the flow through fraction. This showed that the FVIII/vWF complex was excluded from the core of the chromatography media. The FIX activity was below level of quantification in the FT, showing that the smaller FIX protein was removed from the FT and bound to the octylamine ligand in the core.

TABLE 2

Dissolved cryoprecipitate on Capto Core 700 (CC700). FVIII, vWF and FIX activity.
FT = flow through. LOQ = level of quantification (FIX: 30 mIU/mL).

| Sample | Vol (mL) | FVIII (mU/mL) | FVIII (mU) | FVIII (%) | vWF (U/mL) | vWF (U) | vWF (%) | FIX (mIU/mL) | FIX (mU) | FIX (%) |
|---|---|---|---|---|---|---|---|---|---|---|
| Cryoprec | 10.0 | 2854 | 28540 | 100 | 2.90 | 29.0 | 100 | 166 | | |
| CC700 FT | 13.8 | 1655 | 22839 | 80 | 1.60 | 22.1 | 76 | <LOQ | | |

Example 2: Chromatography of Cryoprecipitate on Capto Core 700 (FIG. 1)

Sample

The sample was dissolved cryoprecipitate from human plasma.

Preparation: Frozen plasma was thawed in ice water, in refrigerator, overnight. The cold plasma was centrifuged at 4° C., to pellet the cryoprecipitate. The cryosupernatant was poured off, and the cryoprecipitate was dissolved in 20 mM Na-citrate, 0.15 M NaCl, 2.6 mM CaCl2, pH 7.0, approximately ⅟10 of the original plasma volume. The dissolved cryoprecipitate was filtered through cotton, and applied to the column.

SDS PAGE showed that much of the smaller proteins in the cryoprecipitate, eg albumin, were absent in the FT, and had therefore bound to the octylamine ligand in the core. The presence of vWF in the flow through fraction could be confirmed by LC-MS.

Example 3: Chromatography on Cryoprecipitate on Prototype 59A (FIG. 2)

Sample

The sample was dissolved cryoprecipitate from human plasma.

Preparation: Frozen plasma was thawed in ice water, in refrigerator, overnight. The cold plasma was centrifuged at 4° C., to pellet the cryoprecipitate. The cryosupernatant was poured off, and the cryoprecipitate was dissolved in 20 mM Na-citrate, 0.15 M NaCl, 2.6 mM CaCl2, pH 7.0, approximately 1/10 of the original plasma volume. The dissolved cryoprecipitate was filtered through cotton, and applied to the column.

Buffers and Running Conditions

Chromatography system: ÄKTAexplorer 100
Column: Tricorn 5/50 column with prototype 59A, CV 1 mL.
Flow rate: 0.5 mL/min.
Sample: 2.15 mL cryoprecipitate.
Running buffer: 20 mM Na-citrate, 0.15 M NaCl, 2.6 mM CaCl2, pH 7.0.
Elution buffer: 20 mM Na-citrate, 0.75 M NaCl, 2.6 mM CaCl2, pH 7.0
CIP: 1 M NaOH, 30% isopropanol.

The column was equilibrated with running buffer prior to the sample application. 2.15 mL of dissolved cryoprecipitate was applied to the column, followed by 5 CV of running buffer. The column was eluted with 5 CV of high salt elution buffer, followed by CIP by applying 5 CV of 1 M NaOH, 30% isopropanol. Finally, the CIP solution was washed out by 3 CV of running buffer.

Analyses

The cryoprecipitate, the collected flow through and the high salt eluate were analyzed for FVIII (Chromogenix Coamatic Factor VIII kit), vWF (Technozym vWF:Ag ELISA kit), and FIX activity (ROX Factor IX kit). The fractions were also analyzed by SDS PAGE and LC-MS. Material which bound to the octylamine ligand in the core was eluted with the CIP solution and was not analysed.

Results

See FIG. 2 for chromatogram and Table 3 for activity results and yield calculations. The levels of FVIII, vWF and FIX activity in the flow through were below limits of quantification, indicating that FVIII/vWF and FIX bound to the column. The FIX activity was below level of quantification also in the eluate, showing that the smaller FIX protein bound to the octylamine ligand in the core. FVIII and vWF activity was found in the eluate, showing that FVIII/vWF bound to the Q ligand in the lid and was eluted with high salt. The FVIII and vWF yields in the high salt eluate were 37% and 32%, respectively. This showed that the FVIII/vWF complex was excluded from the core of the chromatography media.

TABLE 3

Dissolved cryoprecipitate on prototype 59A. FVIII, vWF and FIX activity.
FT = flow through. E = eluate. LOQ = level of quantification
(FVIII: 8 mU/mL, vWF: 0.10 U/mL, FIX: 30 mU/mL).

| Sample | Vol (mL) | FVIII (mU/mL) | FVIII (mU) | FVIII (%) | vWF (U/mL) | vWF (U) | vWF (%) | FIX (mU/mL) | FIX (mU) | FIX (%) |
|---|---|---|---|---|---|---|---|---|---|---|
| Cryoprec | 2.15 | 2854 | 6136 | 100 | 2.90 | 6.2 | 100 | 166 | 357 | 100 |
| Prototype 59A FT | 5.0 | <LOQ | | | <LOQ | | | <LOQ | | |
| Prototype 59A E | 5.0 | 460 | 2300 | 37 | 0.40 | 2.0 | 32 | <LOQ | | |

Results from SDS PAGE (not shown) revealed that much of the smaller proteins in the cryoprecipitate, eg albumin, were absent in the FT and eluate fractions, and were therefore bound to the octylamine ligand in the core. The presence of vWF in the eluate could be confirmed by LC-MS (not shown).

The invention claimed is:

1. A chromatographic method for purification of Factor VIII (FVIII) and von Willebrand factor (vWF) from a cryoprecipitate of plasma, comprising the following steps:
    loading the cryoprecipitate on a chromatography column packed with a resin comprising porous lid beads having an inner porous core and an outer porous lid, wherein the inner core is provided with octylamine ligands, wherein the outer porous lid is provided with anion exchange ligands, wherein the total lid bead thickness is 40-100 μm in diameter, and the outer porous lid thickness is 2-10 μm, and wherein a porosity of the lid and a porosity of the core does not allow entering of vWF, does not allow entering of FVIII/vWF complex, and does not allow entering of molecules larger than 500 kD;
    adsorbing FVIII, vWF, or FVIII/vWF complex on said anion exchange ligands;
    adsorbing undesired plasma proteins on the octylamine ligands in the core;
    eluting FVIII, vWF, or FVIII/vWF complex from said anion exchange ligands; and
    collecting FVIII, vWF, or FVIII/vWF complex from the column.

2. The method according to claim 1, wherein the method comprises collecting FVIII and vWF in flow through fractions from the column.

3. The method according to claim 1, wherein the method comprises adsorbing FVIII/vWF complex on said anion exchange ligands in the same step as adsorbing the undesired plasma proteins on the octylamine ligands in the core; and eluting FVIII/vWF complex from said anion exchange ligands.

4. The method according to claim 1, wherein the anion exchange ligands are selected from diethylaminoethyl (DEAE), quaternary aminoethyl (QAE) or quaternary ammonium (Q).

5. The method according to claim 4, wherein the anion exchange ligands are Q-ligands.

6. The method according to claim 1, wherein the ligand concentration in the lid is 10-50 μmole/ml.

7. The method according to claim 1, wherein the ligand concentration in the core is 30-85 μmole/ml.

8. The method according to claim 1, wherein the undesired plasma proteins are human serum albumin (HSA), IgG and Factor IX (FIX).

9. The method according to claim 1, wherein the lid and the core are made of agarose of the same porosity.

10. The method according to claim 1, wherein the porosity of the lid is larger than the porosity of the core.

11. The method according to claim 1, wherein the porosity of the lid is smaller than the porosity of the core.

12. The method according to claim 1, wherein the lid and the core are made of a synthetic polymer material or a natural polymer material.

\* \* \* \* \*